US008283482B2

(12) United States Patent  
Fujimori et al.

(10) Patent No.: US 8,283,482 B2  
(45) Date of Patent: Oct. 9, 2012

(54) METHOD FOR PRODUCING CROSS-COUPLING COMPOUND

(75) Inventors: Taketoshi Fujimori, Haga-gun (JP); Mio Ishita, Haga-gun (JP); Yoshinori Nishizawa, Haga-gun (JP)

(73) Assignee: Kao Corporation, Tokyo (JP)

( * ) Notice: Subject to any disclaimer, the term of this patent is extended or adjusted under 35 U.S.C. 154(b) by 260 days.

(21) Appl. No.: 12/594,726

(22) PCT Filed: Feb. 8, 2008

(86) PCT No.: PCT/JP2008/000181  
§ 371 (c)(1),  
(2), (4) Date: Oct. 5, 2009

(87) PCT Pub. No.: WO2008/129753  
PCT Pub. Date: Oct. 30, 2008

(65) Prior Publication Data  
US 2010/0048929 A1    Feb. 25, 2010

(30) Foreign Application Priority Data

Apr. 4, 2007 (JP) .................................. 2007-098663  
Nov. 1, 2007 (JP) .................................. 2007-285429  
Dec. 19, 2007 (JP) .................................. 2007-327735

(51) Int. Cl.  
*C07C 51/00* (2006.01)

(52) U.S. Cl. ....................................... 554/148; 554/153

(58) Field of Classification Search .................. 554/148, 554/153  
See application file for complete search history.

(56) References Cited

U.S. PATENT DOCUMENTS

| 4,912,276 A | 3/1990 | Puckette | |
|---|---|---|---|
| 2003/0232820 A1* | 12/2003 | Wolfe et al. | ........... 514/228.8 |

FOREIGN PATENT DOCUMENTS

| JP | 48 86801 | | 11/1973 |
|---|---|---|---|
| JP | 4886801 | * | 11/1973 |
| JP | 60 72833 | | 4/1985 |
| JP | 6072833 | * | 4/1985 |
| JP | 60-161946 | | 8/1985 |
| JP | 4 501418 | | 3/1992 |
| JP | 4501418 | * | 3/1992 |
| JP | 5-25108 | | 2/1993 |
| JP | 5 155805 | | 6/1993 |
| JP | 5155805 | * | 6/1993 |
| JP | 6-128193 | | 5/1994 |
| JP | 2008 37852 | | 2/2008 |
| WO | 2006 083030 | | 8/2006 |
| WO | WO 2006083030 | * | 8/2006 |

OTHER PUBLICATIONS

Hassarajani, S. A. et al., Journal of Chemical Research, Synopses, 1993, No. 6, p. 219.*

Hassarajani, S. A. et al., "A Short and Practical Synthesis of 8-Methylnonanoic Acid, A Synthon of Dihydrocapsaicin, Via Grignard Coupling", Journal of Chemical Research, Synopses, No. 6, p. 219 (1993).

Kohei Tamao, et al., "Nickel-Phosphine Complex-Catalyzed Grignard Coupling. I. Cross-Coupling of Alkyl, Aryl and Alkenyl Grignard Reagents with Aryl and Alkenyl Halides: General Scope and Limitations", Bulletin of the Chemical Society of Japan, vol. 49, No. 7, 1976, pp. 1958-1969.

(Continued)

*Primary Examiner* — Deborah D Carr  
(74) *Attorney, Agent, or Firm* — Oblon, Spivak, McClelland, Maier & Neustadt, L.L.P.

(57) ABSTRACT

To provide a method for performing a cross-coupling reaction of a Grignard compound with an alkyl halide simply, efficiently and in high yield, a method for obtaining a ω-bromo long chain carboxylic acid simply and efficiently using an easily obtainable raw material and a method for producing a useful branched fatty acid simply and efficiently Reaction A:

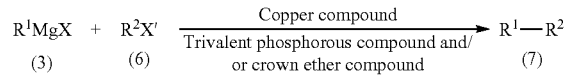

[$R^1$: an alkyl group having 1 to 15 carbon atoms, $R^2$: an alkyl group having 1 to 30 carbon atoms with a carboxyl group and X and X': a halogen atom]

Reaction B:

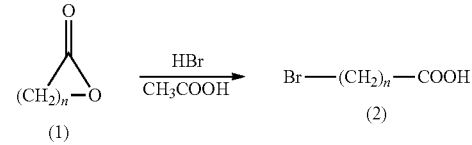

[n: an integer of 9 to 17]

Reaction C:

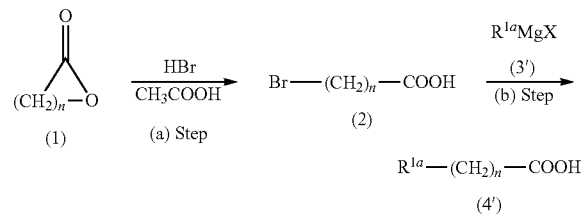

[n: an integer of 9 to 17, $R^{1a}$: a branched alkyl group having 3 to 8 carbon atoms and X: a halogen atom].

21 Claims, No Drawings

OTHER PUBLICATIONS

Jun Terao, et al., "Ni- or Cu-Catalyzed Cross-Coupling Reaction of Alkyl Fluorides with Grignard Reagents" J. Am. Chem. Soc., vol. 125, No. 19, 2003, pp. 5646-5647.

Gérard Cahiez, et al. "Cu-Catalyzed Alkylation of Grignard Reagents: A New Efficient Procedure", Tetrahedron, vol. 56, 2000, pp. 2733-2737.

"Mixed Cuprate Reagents of Type $R_1R_2CuLi$ Which Allow Selective Group Transfer", Journal of the American Chemical Society, vol. 94, No. 20, Oct. 4, 1972, pp. 7210-7211.

Ruthven N. A. H. Lewis, et al., "Thermotropic Phase Behavior of Model Membranes Composed of Phosphatidylcholines Containing $dl$-Methyl Anteisobranched Fatty Acids. 1. Differential Scanning Calorimetric and $^{31}P$ NMR Spectroscopic Studies", Biochemistry, vol. 26, No. 13, 1987, pp. 4036-4044.

Franka Ganske, et al., "Enzyme-Catalyzed Hydrolysis of 18-Methyl Eicosanoic Acid-Cysteine Thioester", Eur. J. Lipid Sci. Technol., vol. 105, pp. 627-632.

Arata Yajima, et al., "Synthesis and Absolute Configuration of MQ-$A_3$ [1-(14'-Methylhexadecanoyl) pyrrolidine], a novel Aliphatic Pyrrolidine Amide from the Tropical Convolvulaceous Species", Biosci. Biotechnol. Biochem, vol. 65, No. 2, 2001, pp. 463-465.

Ted A. Baer, et al., "Copper Catalyzed Reaction of Grignard Reagents with Chloramagnesium Salts of ω-Bromoacids", Tetrahedron Letters No. 51, 1976, pp. 4697-4700.

Nestor Carballeira, et al., "Biosynthetic Studies of Marine Lipids. 5.[1] The Biosynthesis of Long-Chain Branched Fatty Acids in Marine Sponges", J. Org. Chem., vol. 51, No. 14, 1986, pp. 2751-2756.

ω- Pentadecalactone, 15-Hydroxypentadecanoic acid, ω-lactone, "Pentalide", "Thibetolide", "Exolide" Synthetic perfumes, The Chemical Daily Co., Ltd. pp. 400-401, with partial translation, 1935.

Toshio Sato, et al., "A Simple Method for the Synthesis of Exaltolide", The Chemical Society of Japan, Bull. Chem. Soc. Jpn., vol. 54, No. 3, Mar. 1981, pp. 945-946.

Tim W. Davey, et al., "Synthesis of ω-Hydroxy Quaternary Ammonium Bolaform Surfactants", Aust. J. Chem., vol. 51, 1998, pp. 581-586.

Andrzej Duda, et al., "Kinetics of the Ring-Opening Polymerization of 6-. 7-, 9-, 12-, 13-, 16-, and 17-Membered Lactones. Comparison of Chemical and Enzymatic Polymerizations," Macromolecules 2002, 35, (4266-4270).

Michael B. Smith, et al., March's Advanced Organic Chemistry Reactions, Mechanisms, and Strucutre, $5^{th}$ Ediition, 2001, (1214).

* cited by examiner

METHOD FOR PRODUCING CROSS-COUPLING COMPOUND

FIELD OF THE INVENTION

The present invention relates to a method for producing a cross-coupling compound and a method for producing a branched fatty acid using the same.

BACKGROUND OF THE INVENTION

A cross-coupling reaction of a Grignard compound with an alkyl halide is employed for various reactions for generating a carbon-carbon bond.

For this reaction to generate a carbon-carbon bond, a transition metal compound such as palladium, nickel and copper is generally used as a catalyst. In addition, there are many reports showing that reaction yield for across-coupling reaction is improved by combination of these transition metal compounds and various additives. Specifically, it is presently known that yield is improved by using phosphine with a nickel catalyst or a palladium catalyst (Non-patent Document 1), or by using a copper catalyst with olefins such as 1,3-butadiene (Non-patent Document 2).

Further, a method of improving reaction yield by adding polar substances has also been reported. For example, it has been reported that yield for cross-coupling using dilithium tetrachloro cuprate catalyst can be improved when a polar solvent such as N-methylpyrrolidinone is added in an excess amount (i.e., 4 to 6 equivalents) relative to a Grignard compound (Non-patent Document 3), or solubility of a n-propylethynyl copper reagent in ether (solvent) and reaction yield are improved when two equivalents of hexamethyl phosphorous triamide is added for synthesizing an organolithium reagent from a n-propylethynyl copper reagent (Non-patent Document 4).

A branched fatty acid is widely used as additives for an industrial product, intermediate materials, and raw materials for cosmetics and perfumes. For example, isostearic acid having an excellent property such as emulsifying property is incorporated in various cosmetics and perfumes. Further, along chain anteiso fatty acid, which is a branched fatty acid present on the surface of human hair, is a useful fatty acid as being capable of protecting hair and providing hair with smooth feeling.

However, the long chain anteiso fatty acid having such important properties is mainly extracted from wool and used. Since isolation of a specific long chain anteiso fatty acid is a very difficult process, its use is limited to a mixture containing them.

As for a method for the selective production of a branched fatty acid, the cross-coupling reaction as described above, and a method based on reaction for generating a carbon-carbon bond as exemplified below have been reported. However, these methods are not all industrially convenient and they cannot be performed at low cost.

(I) A method including reacting dihaloalkane with haloalkyl magnesium in the presence of a copper catalyst such as dilithium tetrachloro cuprate and subsequently carboxylating the terminal group (Patent Document 1), and a method including reacting dicarboxylic monoester with an organic cadmium compound and reducing the resulting keto acid (Non-patent Document 5).

These methods are problematic in that, as including a step of converting selectively one of two identical functional groups, yield is low. Further, although another method in which one of the two identical functional groups is protected with a protecting group and reacted has been reported (Non-patent Document 6), it is also problematic in that the number of the required reaction processes is big and operation is roundabout.

(II) A reaction for generating a carbon-carbon bond between two kinds of a Grignard compound and halocarboxylic acid (Non-patent Document 7).

Because two kinds of a Grignard compound are used, this method is problematic in that general applicability of a substrate is low, and it is unfavorable in terms of production cost. In addition, while it is believed that 11-bromoundecanoic acid as halocarboxylic acid used is synthesized from 10-undecenoic acid, descriptions or method of obtaining halocarboxylic acids having eleven or more carbon atoms is not included and production of a long chain branched fatty acid is not established.

(III) A method based on Wittig reaction i) A method in which an aldehyde and a phosphonium salt obtained from diol are subjected to a Wittig reaction followed by reduction and carboxylation of the terminal group (Non-patent Document 8).

ii) A method in which an aldehyde and a branched alkyl phosphonium salt that is represented by the following formula (Y) are subjected to a Wittig reaction followed by reduction and hydrolysis (Patent Document 2).

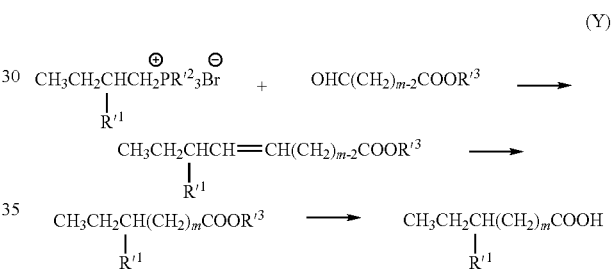

(In the formula, $R'^1$ represents a methyl group or an ethyl group, $R'^2$ represents a saturated or unsaturated hydrocarbon group, $R'^3$ represents an alkyl group or an alkenyl group having 1 to 6 carbon atoms and m represents an integer of 4 to 16.)

iii) A method in which ω-phosphonium fatty acid ester represented by the following formula (Z) and a branched aldehyde are subjected to a Wittig reaction in the presence of a base such as sodium methylate followed by reduction and hydrolysis in the presence of a basic catalyst (Patent Document 3).

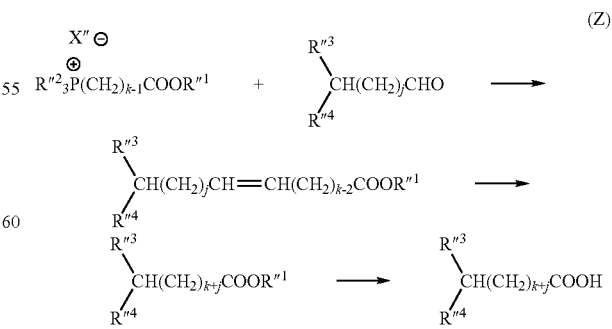

(In the formula, $R'''^1$ represents an alkyl group or an alkenyl group having 1 to 6 carbon atoms, $R''^2$ represents a saturated or unsaturated hydrocarbon group, $R'''^3$ and $R'''^4$ respectively represent a methyl group or an ethyl group, X" represents a halogen atom, k represents a number of 5 to 16 and j represents a number of 0 or 1.)

However, these methods including the Wittig reaction are problematic in that reaction steps are too many and a great amount of phosphine oxide is produced as byproduct.

(IV) A method in which a carboxylic ester is produced from a Grignard compound and a halocarboxylic ester in the presence of copper compound followed by hydrolysis to obtain a branched fatty acid (Patent Document 4).

According to this method, a side reaction between an ester and a Grignard compound occurs in addition to a desired cross-coupling reaction. As such, not only yield is lowered but also separation of a byproduct remains as a problem.

Meanwhile, with respect to a ω-halo long chain carboxylic acid which is useful as a starting material for producing a branched fatty acid, etc., a method of producing 15-bromopentadecanoic acid by Kolbe electrolysis of azelaic acid, forming half salts of Ag, and bromination (Non-patent Document 9) and a method of producing 15-bromopentadecanoic acid by reacting 15-methoxypentadecanoic acid with boron tribromide (Non-patent Document 10) and the like have been previously reported. However, these methods all require many steps, and therefore are not a method for convenient synthesis.

In addition, a method in which 15-bromopentadecanoic acid can be obtained in high yield from 15-pentadecanolide (trade name Pentalide) by using conc. sulfuric acid-hydrogen bromide acid has been reported recently (Non-patent Document 11). However, according to this method, there are some problems such that the reaction system becomes blackened, or insoluble matters are produced and cannot be separated easily from an aqueous layer so that refluxing for a long period of time like 3.5 days is required. As such, it is not applicable for actual synthesis.

[Non-patent Document 1] Bull. Chem. Soc. Jpn., 1976, 49, 1958-1969
[Non-patent Document 2] J. Am. Chem. Soc., 2003, 125, 5646-5647
[Non-patent Document 3] Tetrahedron, 2000, 56, 2733-2737
[Non-patent Document 4] J. Am. Chem. Soc., 1972, 94, 7210-7211
[Non-patent Document 5] Biochemistry, 1987, 26, 4636-4044
[Non-patent Document 6] Eur. J. Lipid Sci. Technol. 2003, 105, 627-632, Biosci. Biotechnol. Biochem. 2001, 65(2), 463-465
[Non-patent Document 7] Tetrahedron Lett., 1976, 51, 4697-4700
[Non-patent Document 8] J. Org. Chem., 1986, 51, 2751-2756
[Non-patent Document 9] Synthetic perfumes, The Chemical Daily Co., Ltd.
[Non-patent Document 10] Bull. Chem. Soc. Jap., 54(3), 945, 1981
[Non-patent Document 11] Aust. J. Chem. 51, 581-586, 1998
[Patent Document 1] JP-A-S60-161946
[Patent Document 2] JP-A-H05-025108
[Patent Document 3] JP-A-H06-128193
[Patent Document 4] WO 2006/083030

SUMMARY OF THE INVENTION

The present invention is related to the following 1) to 3).
1) A method for producing cross-coupling compounds represented by the following formula (7): $R^1$—$R^2$ [wherein, $R^1$ represents an alkyl group having 1 to 15 carbon atoms and $R^2$ represents an alkyl group having 1 to 30 carbon atoms with a carboxyl group], including across-coupling reaction of a Grignard compound represented by the following formula (3): $R^1MgX$ [wherein, $R^1$ is as defined in the above] with an alkyl halide represented by the following formula (6): $R^2$—X' [wherein, $R^2$ is as defined in the above] in the presence of a copper compound and a trivalent phosphoric acid compound and/or a crown ether compound.

2) A method for producing a ω-bromo long chain carboxylic acid represented by the following formula (2): Br—$(CH_2)_n$—$CO_2H$ [wherein, n represents an integer of 9 to 17], including reacting cyclic esters represented by the following formula (1)

(1)

[wherein, n is as defined in the above]
with hydrogen bromide in acetic acid solvent.

3) A method for producing a branched fatty acid having 13 to 26 carbon atoms represented by the following formula (4'): $R^{1a}$—$(CH_2)_n$—$CO_2H$ [wherein, $R^{1a}$ represents a branched alkyl group having 3 to 8 carbon atoms and n represents an integer of 9 to 17], including
(a) reacting cyclic esters represented by the following formula (1)

(1)

[wherein, n is as defined in the above]
with hydrogen bromide in acetic acid solvent to obtain bromocarboxylic acid represented by the following formula (2): Br—$(CH_2)_n$—$CO_2H$ [wherein, n is as defined in the above], and then (b) reacting the bromocarboxylic acid with a Grignard compound represented by the following formula (3'): $R^{1a}MgX$ [wherein, $R^{1a}$ is as defined in the above and X represents a halogen atom].

DETAILED DESCRIPTION OF THE INVENTION

The present invention relates to the followings: 1) to provide a method for performing a cross-coupling reaction of a Grignard compound with an alkyl halide simply, efficiently and in high yield, 2) to provide a method for obtaining a ω-bromo long chain carboxylic acid simply and efficiently using an easily obtainable raw material, and 3) to provide a method for producing a useful branched fatty acid simply and efficiently.

As a result of intensive studies regarding a method that is most useful for industrial synthesis, inventors of the present invention found that, by subjecting a Grignard compound and an alkyl halide to a cross-coupling reaction in the presence of a copper compound and a trivalent phosphorus compound which is not a polar substance, and/or a crown ether compound that is widely used as a phase transfer catalyst, a cross-coupling compound can be produced simply and efficiently.

Further, as a result of studying a method for producing a ω-halo long chain carboxylic acid by using cyclic esters, the present inventors found that, a ω-bromo long chain carboxylic acid can be produced quantitatively without generating byproducts, etc. by acting hydrogen bromide in the acetic acid solvent.

Still further, the present inventors found that a branched fatty acid can be produced with two steps by using industrially available cyclic esters.

According to the present invention, a cross-coupling compound of a Grignard compound and an alkyl halide can be produced simply and efficiently, and in particular, a branched fatty acid such as 18-methyl eicosanoic acid, which is useful as a hair care material, can be produced simply and efficiently from a Grignard compound and a halocarboxylic acid.

Further, according to the present invention, by using easily obtainable cyclic esters that are useful as an intermediate for synthesis of a branched fatty acid, a ω-bromo long chain carboxylic acid can be produced quantitatively. Since this method can be carried out in short time, blackening of the reaction system or generation of insoluble matters or byproducts is avoided, and therefore the post-treatment process is rather simple. Thus, it is useful as an industrial method for producing a ω-bromo long chain carboxylic acid, which is a starting material for preparing surfactants, etc.

Still further, according to the present invention, the branched fatty acid can be produced simply and efficiently from industrially available starting materials. In particular, this method is useful as an industrial method for preparing branched fatty acids such as iso fatty acids and anteiso fatty acids that are useful as an agent for improving hair feel.

(A) Preparation of a Cross-coupling Compound

The method for producing a cross-coupling compound according to the present invention is shown with the following reaction scheme (Reaction (A)),

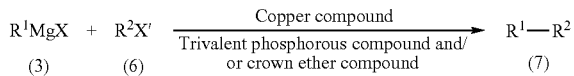

[wherein, $R^1$ represents an alkyl group having 1 to 15 carbon atoms, $R^2$ represents an alkyl group having 1 to 30 carbon atoms with a carboxyl group, and X and X' represent a halogen atom].

Copper compound which can be used for the present reaction is not specifically limited. Any copper compound which is typically used for the reaction for generating a carbon-carbon bond can be used. Examples thereof include copper halide, lithium copper compound and the like, including copper bromide (I), copper bromide (II), copper chloride (I), copper chloride (II), copper iodide (I), copper iodide (II), dilithium tetrachlorocuprate. Among these, copper halide and dilithium tetrachlorocuprate are preferred. Copper halide is more preferred. Further, as for a copper halide, copper bromide (I) and copper chloride (I) are preferred. Copper bromide (I) is more preferred.

As for a trivalent phosphorous compound, those typically used as a phosphorous (III) catalyst are preferred. Examples include phosphines, phosphites, phosphonites, phosphinites and the like. Phosphines and phosphites are preferred.

As for phosphines, a phosphine that is represented by the following formula (8): $R^3{}_3P$ [wherein, $R^3$ represents an alkyl group having 1 to 6 carbon atoms; a cyclohexyl group; or a phenyl group which may have a methyl group or a methoxy group] is preferred. Trimethyl phosphine, triphenyl phosphine, tritolyl phoshpine, and trimethoxyphenyl phosphine are more preferred.

An alkyl group having 1 to 6 carbon atoms that is represented by $R^3$ can be any of a linear and branched chain. However, a linear alkyl group having 1 to 4 carbon atoms is preferred. A methyl group, an ethyl group, an n-propyl group, and an n-butyl group are more preferred. A methyl group is even more preferred.

As for a phenyl group which may have a methyl group or a methoxy group that is represented by $R^3$, a phenyl group, a p-methylphenyl group, and a p-methoxyphenyl group are preferred.

As for phosphites, a phosphite that is represented by the following formula (9) is preferred: $(R^4O)_3P$ [wherein, $R^4$ represents an alkyl group having 1 to 4 carbon atoms]. Triethoxyphosphite is more preferred.

An alkyl group having 1 to 4 carbon atoms that is represented by $R^4$ can be any of a linear or branched chain. However, a linear chain is preferred. A methyl group, an ethyl group, an n-propyl group, and an n-butyl group are more preferred. An ethyl group is even more preferred.

As for the crown ether compounds according to the present invention, in addition to 18-crown-6, 15-crown-5, 12-crown-4, 30-crown-10 and the like; benzo crown such as benzo-18-crown-6, dibenzo-18-crown-6, tribenzo-18-crown-6, benzo-15-crown-5, dibenzo-15-crown-5, tribenzo-15-crown-5, benzo-12-crown-4, dibenzo-12-crown-4, tribenzo-12-crown-4, benzo-30-crown-10, dibenzo-30-crown-10, tribenzo-30-crown-10, and; cyclohexano crown such as dicyclohexano-18-crown-6, dicyclohexano-15-crown-5, dicyclohexano-12-crown-4, dicyclohexano-30-crown-10 can be mentioned. In terms of efficiency of reaction for generating a carbon-carbon bond, 18-crown-6, 15-crown-5, and dibenzo-18-crown-6 are preferred.

In addition, these crown ethers can be used as a mixture containing at least two of them.

In addition, these crown ethers can be obtained by a known method for synthesis of ether such as subjecting an alkyl halide to a reaction with sodium alkoxide, or a commercially available product can be used.

As for the Grignard compound that is represented by the formula (3), an alkyl group having 1 to 15 carbon atoms that is represented by $R^1$ can be any of a linear or branched chain. Examples include a methyl group, an ethyl group, a propyl group, an isopropyl group, a butyl group, a hexyl group, a pentyl group, an iso-propyl group, a 2-methylpropyl group, an isobutyl group, a tert-butyl group, a sec-butyl group, a 2-methylbutyl group, a 3-methyl butyl group, a 2-methylpentyl group, a 3-methylpentyl group, a 4-methylpentyl group, a 4-methylhexyl group, a 5-methylhexyl group, a 5-methylheptyl group, a 6-methylheptyl group. Among these, a branched alkyl group having 3 to 6 carbon atoms is preferred. A 2-methylpropyl group, an iso-propyl group, and a sec-butyl group are more preferred. A sec-butyl group is even more preferred.

As for a halogen atom that is represented by X, a chlorine atom, a bromine atom and an iodine atom can be mentioned. A chlorine atom and a bromine atom are preferred. A bromine atom is more preferred.

As for the Grignard compound that is represented by the formula (3), sec-butyl magnesium bromide, iso-propyl magnesium bromide, 2-methylpropyl magnesium bromide, 2-methylbutyl magnesium bromide, 3-methylpentyl magnesium bromide, 3-methylbutyl magnesium bromide, 4-methylpentyl magnesium bromide, tert-butyl magnesium bromide, 2-methylpentyl magnesium bromide, 4-methylhexyl magnesium bromide, 5-methylhexyl magnesium bromide, 5-methylheptyl magnesium bromide, 6-methylheptyl magnesium bromide, sec-butyl magnesium chloride, iso-propyl magnesium chloride, 2-methylpropyl magnesium chloride, 2-methylbutyl magnesium chloride, 3-methylpentyl magnesium chloride, 3-methylbutyl magnesium chloride, 4-methylpentyl magnesium chloride, tert-butyl magnesium chloride, 2-methylpentyl magnesium chloride, 4-methylhexyl magnesium chloride, 5-methylhexyl magnesium chloride, 5-methylheptyl magnesium chloride, 6-methylheptyl magnesium chloride and the like can be mentioned, sec-butyl magnesium bromide, iso-propyl magnesium bromide, 2-methylpropyl magnesium bromide, 2-methylbutyl magnesium bromide, 3-methylpentyl magnesium bromide, 3-methylbutyl magnesium bromide, and 4-methylpentyl magnesium bromide are preferred, sec-butyl magnesium bromide, iso-propyl magnesium bromide, and 2-methylpropyl magnesium bromide are more preferred, and sec-butyl magnesium bromide is even more preferred. These Grignard compounds can be synthesized from corresponding alkyl halides according to a known method.

As for an alkyl halide that is represented by the formula (6), an alkyl group having 1 to 30 carbon atoms with a carboxyl group represented by $R^2$ can be any of a linear or branched chain. Examples thereof include a carboxymethyl group, a carboxybutyl group, a carboxyhexyl group, a carboxyoctyl group, a carboxydecyl group, a carboxyundecyl group, a carboxydodecyl group, a carboxytridecyl group, a carboxytetradecyl group, a carboxypentadecyl group, a carboxyhexadecyl group, a carboxyheptadecyl group and the like. Among these, a linear chain having 5 to 20 carbon atoms is preferred. A carboxyundecyl group, a carboxydodecyl group, a carboxytridecyl group, a carboxytetradecyl group, a carboxypentadecyl group, a carboxyhexadecyl group, and a carboxyheptadecyl group are more preferred. A carboxypentadecyl group is even more preferred.

As for a halogen atom that is represented by X', a fluorine atom, a chlorine atom, a bromine atom and an iodine atom can be mentioned. A bromine atom is preferred.

As for an alkyl halide that is represented by $R^2$—X', 11-bromoundecanoic acid, 12-bromododecanoic acid, 13-bromotridecanoic acid, 14-bromotetradecanoic acid, 15-bromopentadecanoic acid, 16-bromohexadecanoic acid, and 17-bromoheptadecanoic acid are preferred. 15-Bromopentadecanoic acid and 16-bromohexadecanoic acid are more preferred.

In addition, the alkyl halide that is represented by $R^2$—X' can be synthesized, for example, by a known method such as bromination of a hydroxy fatty acid with hydrogen bromide acid or a mixture containing hydrogen bromide acid and sulfuric acid, etc. A commercially available product can be also used.

The reaction can be carried out in the presence or absence of a solvent. However, for promoting a smooth reaction of generating a carbon-carbon bond, it is preferably carried out in the presence of a solvent.

The solvent is not specifically limited. Examples thereof include ethers such as tetrahydrofuran, diethyl ether, dimethyl ether, methoxy ethane, 1,2-dimethoxy ethane, t-butyl-methyl ether, isopropyl ether, dioxane and cyclopentylmethyl ether; hydrocarbons such as hexane, cyclohexane, heptane, isooctane and decane; alcohols such as t-butanol, methanol, ethanol, isopropanol and n-butanol; aromatic hydrocarbons such as benzene, toluene and xylene; ketones such as acetone and nitriles such as acetonitrile, and their mixture.

When a trivalent phosphorous compound is used for the reaction of the present invention, use amount of the Grignard compound that is represented by the above formula (3), a metal catalyst, and a trivalent phosphorous compound can be appropriately chosen so as not to delay the reaction time or reduce the reaction rate. Preferably, relative to the alkyl halide that is represented by the above formula (6), they are used in an amount of 1 to 4 equivalents, 0.001 to 1 equivalents, and 0.0001 to 10 equivalents, respectively.

When the crown ether is used for the reaction of the present invention, use amount of the Grignard compound that is represented by the above formula (3), a metal catalyst, and the crown ether can be appropriately chosen so as not to delay the reaction time or reduce the reaction rate. Preferably, relative to the alkyl halide that is represented by the above formula (6), they are used in an amount of 1 to 4 equivalents, 0.001 to 1 equivalents, and 0.0001 to 10 equivalents, respectively.

Reaction temperature is between −20° C. and 60° C., for example, and reaction time is between 30 minutes and 50 hours, for example.

For promoting a smooth reaction of generating a carbon-carbon bond, the reaction is preferably carried out under inert gas atmosphere. The inert gas is not specifically limited. For example, argon gas, nitrogen gas, helium gas and the like can be mentioned.

As a result, according to the reaction of the present invention, a cross-coupling compound such as 10-methyldodecanoic acid, 11-methyldodecanoic acid, 11-methyltridecanoic acid, 12-methyltridecanoic acid, 12-methyltetradecanoic acid, 13-methyltetradecanoic acid, 13-methylpentadecanoic acid, 14-methylpentadecanoic acid, 14-methylhexadecanoic acid, 15-methylhexadecanoic acid, 15-methylheptadecanoic acid, 18-methylnonadecanoic acid, 19-methyleicosanoic acid, 19-methylheneicosanoic acid, 20-methylheneicosanoic acid, 20-methyldocosanoic acid, 21-methyldocosanoic acid, 21-methyltricosanoic acid, 22-methyltricosanoic acid, 22-methyltetracosanoic acid, 23-methyltetracosanoic acid, 23-methylpentacosanoic acid, 24-methylpentacosanoic acid, 24-methylhexacosanoic acid, 25-methylhexacosanoic acid, 16-methylheptadecanoic acid, 16-methyloctadecanoic acid, 17-methyloctadecanoic acid, 17-methylnonadecanoic acid, 18-methyleicosanoic acid can be produced efficiently. Among these, preferably 16-methylheptadecanoic acid, 16-methyloctadecanoic acid, 17-methyloctadecanoic acid, 17-methylnonadecanoic acid, and 18-methyleicosanoic acid can be produced more efficiently.

The target compound can be separated by isolation and purification from a reaction system, based on an appropriate combination of general means such as filtering, washing, drying, recrystallization, centrifugation, extraction using various solvents, distillation and chromatography.

(B) Preparation of a ω-bromo Long Chain Carboxylic Acid

The method for producing the ω-bromo long chain carboxylic acid of the present invention is shown with the following reaction scheme (Reaction (B)),

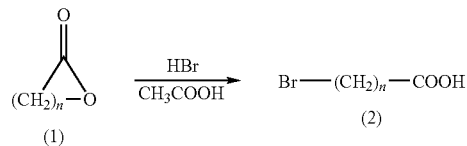

[wherein, n represents an integer of 9 to 17].

In the formula, n represents an integer of 9 to 17, preferably it is an integer of 11 to 15, and more preferably it is an integer of 14 or 15.

According to the reaction, by using cyclic esters such as 15-pentadecanolide, 16-hexadecanolide, 12-dodecanolide, 10-decanolide, 11-undecanolide, 13-tridecanolide, 14-tetradecanolide, 17-heptadecanolide and 18-octadecanolide, a bromocarboxylic acid such as 15-bromopentadecanoic acid, 16-bromohexadecanoic acid, 12-bromododecanoic acid, 10-bromodecanoic acid, 11-bromoundecanoic acid, 13-bromotridecanoic acid, 14-bromotetradecanoic acid, 17-bromoheptadecanoic acid and 18-bromooctadecanoic acid can be prepared. As for the cyclic esters, 15-pentadecanolide, 16-hexadecanolide and 12-dodecanolide are preferably used. More preferably, 15-pentadecanolide and 16-hexadecanolide are used.

The present reaction can be carried out in the presence of acetic acid and can be performed by using acetic acid as a solvent. As described in the above Non-patent Document 11, when concentrated sulfuric acid-hydrogen bromide acid is used and 15-pentadecanolide is reacted, for example, 15-(15-bromopentadecyloxy)pentadecanoic acid, which is difficult to get separated from the target compound 15-bromopentadecanoic acid, is produced as a byproduct. As a result, it becomes difficult to obtain highly pure 15-bromopentadecanoic acid.

In this case, the use amount of acetic acid is preferably 0.1 to 10 times the amount of cyclic esters. More preferably, it is 0.5 to 5 times the amount of cyclic esters.

Further, other solvent can be used with acetic acid. It is preferable that only acetic acid is used as a solvent.

Examples of other solvent include ethers such as tetrahydrofuran, diethyl ether, dimethyl ether, methoxyethane, 1,2-dimethoxy ethane, t-butylmethyl ether, isopropyl ether, dioxane and cyclopentylmethyl ether; hydrocarbons such as hexane, cyclohexane, heptane, isooctane and decane; aromatic hydrocarbons such as benzene, toluene and xylene and a mixture thereof.

Hydrogen bromide is preferably used in an amount of 1 to 3 moles per one mole of the cyclic esters. More preferably, it is used in an amount of 1.0 to 2.0 moles per one mole of the cyclic esters.

Since the reaction of the present invention can be performed almost quantitatively when it is carried out in a closed system, the reaction is preferably carried out in a closed system. In addition, even in an open system, by employing excess amount of hydrogen bromide using an apparatus equipped with a condenser tube, the target compound can be obtained with yield of about 50% (see, Example B-3). With respect to a closed-system reaction apparatus, a heat-proof and pressure-proof apparatus such as an autoclave can be used. An apparatus having a stirring means located in it is preferable.

Reaction temperature for the reaction is preferably in the range of 10° C. to 150° C., and more preferably in the range of 50° C. to 130° C.

Reaction time of the reaction is preferably from 1 to 50 hours, more preferably 5 to 25 hours.

If necessary, the ω-bromo long chain carboxylic acid that is obtained accordingly can be purified and isolated by a purification method that is generally used in a field of organic synthetic chemistry, such as filtering, washing, drying, recrystallization, extraction using various solvents, distillation, various kinds of chromatography.

(C) Preparation of a Branched Fatty Acid

The method for producing the branched fatty acid of the present invention is shown with the following reaction scheme (Reaction (C)),

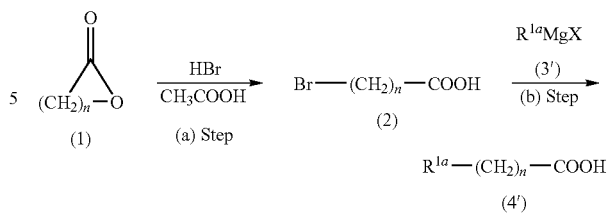

[wherein, n represents an integer of 9 to 17, $R^{1a}$ represents a branched alkyl group having 3 to 8 carbon atoms, and X represents a halogen atom].

1. Step (a)

Step (a) is a reaction to obtain the bromocarboxylic acid that is represented by the formula (2) by reacting the cyclic esters that are represented by the formula (1) with hydrogen bromide in acetic acid solvent.

In the formulae (1), (2) and (4) of the present invention, n represents an integer of 9 to 17, preferably it is an integer of 11 to 15, more preferably an integer of 14 or 15.

Step (a) is a reaction which is the same as the Reaction (B) described above.

2. Step (b)

Step (b) is a reaction to obtain the branched fatty acid that is represented by the formula (4') by reacting the bromocarboxylic acid of the formula (2), as obtained from the above Step (a), with the Grignard compound of the formula (3') (i.e., cross-coupling reaction).

Examples of the branched alkyl group having 3 to 8 carbon atoms in the formula (3') as represented by $R^{1a}$ include an iso-propyl group, a 2-methylpropyl group, a tert-butyl group, a sec-butyl group, a 2-methylbutyl group, a 3-methylbutyl group, a 2-methylpentyl group, a 3-methylpentyl group, a 4-methylpentyl group, a 4-methylhexyl group, a 5-methylhexyl group, a 5-methylheptyl group, a 6-methylheptyl group. Among these, a branched alkyl group having 3 to 6 carbon atoms is preferable. A 2-methylpropyl group, an iso-propyl group and a sec-butyl group are more preferable and a sec-butyl group is even more preferable.

As for the halogen atom that is represented by X in the formula (3'), a chlorine atom, a bromine atom and an iodine atom can be mentioned. A chlorine atom and a bromine atom are preferable. A bromine atom is more preferable.

As for the Grignard compound that is represented by the formula (3'), sec-butyl magnesium bromide, iso-propyl magnesium bromide, 2-methylpropyl magnesium bromide, 2-methylbutyl magnesium bromide, 3-methylpentyl magnesium bromide, 3-methylbutyl magnesium bromide, 4-methylpentyl magnesium bromide, tert-butyl magnesium bromide, 2-methylpentyl magnesium bromide, 4-methylhexyl magnesium bromide, 5-methylhexyl magnesium bromide, 5-methylheptyl magnesium bromide, 6-methylheptyl magnesium bromide, sec-butyl magnesium chloride, iso-propyl magnesium chloride, 2-methylpropyl magnesium chloride, 2-methylbutyl magnesium chloride, 3-methylpentyl magnesium chloride, 3-methylbutyl magnesium chloride, 4-methylpentyl magnesium chloride, tert-butyl magnesium chloride, 2-methylpentyl magnesium chloride, 4-methylhexyl magnesium chloride, 5-methylhexyl magnesium chloride, 5-methylheptyl magnesium chloride, 6-methylheptyl magnesium chloride and the like can be mentioned. Sec-butyl magnesium bromide, iso-propyl magnesium bromide, 2-methylpropyl magnesium bromide, 2-methylbutyl magnesium bromide, 3-methylpentyl magnesium bromide, 3-methylbutyl magnesium bromide and 4-methylpentyl magnesium bromide are preferable. Sec-butyl magnesium bromide, iso-propyl magnesium bromide and 2-methylpropyl magnesium bromide are more preferable. Sec-butyl magnesium bromide is even more preferable. These Grignard compounds can be synthesized from corresponding alkyl halides based on a known method.

The cross-coupling reaction for the present step can be carried out in the absence or the presence of a metal catalyst if it is carried out under a typical condition that is employed for a reaction for generating a carbon-carbon bond. However, in terms of the efficiency of a reaction, it is preferably carried out in the presence of a metal catalyst.

Examples of a metal catalyst include a copper compound, a palladium compound, a nickel compound, a zinc compound, a tin compound, an iron compound, an aluminum compound, a rhodium compound and a ruthenium compound. For promoting a smooth reaction for generating a carbon-carbon bond, a copper compound is preferable.

As for the copper compound, those exemplified above for the Reaction (A) can be also used.

Further, for promoting a smooth reaction for generating a carbon-carbon bond, the cross-coupling reaction of the present step is preferably carried out in the presence of a trivalent phosphorous compound and/or crown ether. More preferably, it is carried out in the presence of a metal catalyst, a trivalent phosphorous compound and/or crown ether. Even more preferably, it is carried out in the presence of a metal catalyst and a trivalent phosphorous compound or in the presence of a metal catalyst and crown ether.

As for the trivalent phosphorous compound and the crown ether compound that are used for the present step, those exemplified above for the Reaction (A) can be mentioned.

The present step can be carried out in the absence or the presence of a solvent. For promoting a smooth reaction for generating a carbon-carbon bond, it is preferably carried out in the presence of a solvent.

As for the solvent, those exemplified above for the Reaction (A) can be also used.

The reaction temperature and the reaction time for Step (b) of the present invention are the same as those described above for the Reaction (A).

For promoting a smooth reaction for generating a carbon-carbon bond, the present step is preferably carried out under an inert gas atmosphere. The inert gas is not specifically limited and examples include argon gas, nitrogen gas, helium gas and the like.

According to the present step, the bromocarboxylic acid that is obtained from the Step (a) can be isolated or used without any isolation. It is preferably isolated and then used.

The target compound can be separated by isolation and purification from a reaction system, based on an appropriate combination of general means such as filtering, washing, drying, recrystallization, centrifugation, extraction using various solvents, distillation and chromatography.

Consequently, according to the Step (a) and the Step (b), a branched fatty acid such as 10-methyldodecanoic acid, 11-methyldodecanoic acid, 11-methyltridecanoic acid, 12-methyltridecanoic acid, 12-methyltetradecanoic acid, 13-methyltetradecanoic acid, 13-methylpentadecanoic acid, 14-methylpentadecanoic acid, 14-methylhexadecanoic acid, 15-methylhexadecanoic acid, 15-methylheptadecanoic acid, 18-methylnonadecanoic acid, 19-methyleicosanoic acid, 19-methylheneicosanoic acid, 20-methylheneicosanoic acid, 20-methyldocosanoic acid, 21-methyldocosanoic acid, 21-methyltricosanoic acid, 22-methyltricosanoic acid, 22-methyltetracosanoic acid, 23-methyltetracosanoic acid, 23-methylpentacosanoic acid, 24-methylpentacosanoic acid, 24-methylhexacosanoic acid, 25-methylhexacosanoic acid, 16-methylheptadecanoic acid, 16-methyloctadecanoic acid, 17-methyloctadecanoic acid, 17-methylnonadecanoic acid, 18-methyleicosanoic acid can be efficiently produced. Among these, preferably 16-methylheptadecanoic acid, 16-methyloctadecanoic acid, 17-methyloctadecanoic acid, 17-methylnonadecanoic acid and 18-methyleicosanoic acid can be more efficiently produced.

EXAMPLES

Hereinbelow, detailed explanations of the reaction are given in view of the Examples.

Products of the reactions of the present invention were compared and identified in view of a standard synthesized separately by the methods already known in literature by gas chromatography and $^1$H-NMR.

Example A1-1

Preparation of 16-methyloctadecanoic acid

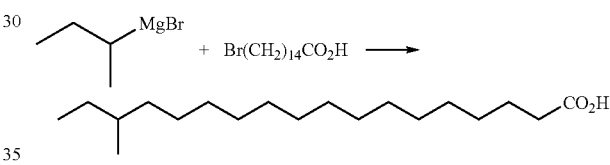

To a four-necked 50 mL of flask equipped with a refluxing condenser tube, a 10 mL of dropping funnel, a magnetic stirrer and a temperature sensor, 15-bromopentadecanoic acid of 800 mg (2.5 mmol) and triphenyl phosphine (Kanto Chemical Co., Inc.) of 3.9 mg (0.006 eq) were added and dried under reduced pressure. Under argon atmosphere, copper bromide (I) (Aldrich Corporation) of 11 mg (0.03 eq) and anhydrous tetrahydrofuran of 1 mL were added to dissolve the materials. At room temperature, 5.5 mL (3 eq) of solution containing 1.36N sec-butyl magnesium bromide/tetrahydrofuran was added dropwise thereto over one hour. After stirring for one hour, 10 mL of 1N aqueous hydrochloric acid solution was added and the extraction was carried out twice by using 50 mL of hexane. After washing twice with 10 mL of ion exchange water, the mixture was dried over magnesium sulfate. After the filtration, the crude product (726 mg) was obtained by concentration under reduced pressure.

Quantitation was carried out based on gas chromatography (column: Ultra-2, 30 m×0.2 mm×0.33 µm, DET 300° C., INJ 300° C., column temperature 100° C.→300° C., 10° C./min) using octadecane as an internal standard. As a result, the yield was 93%.

Example A1-2 to A1-13

Preparation of 16-methyloctadecanoic acid

16-Methyloctadecanoic acid was produced in the same manner as Example A1-1 except that the copper compounds and the phosphines or phosphites described in Table 1 below were used.

TABLE 1

| Example | Use amount of a Grignard compound* | Copper compound Type | Addition amount* | Phosphine or phosphite Type | Addition amount* | Reaction temperature (°C.) | Yield (%) |
|---|---|---|---|---|---|---|---|
| A1-2 | 4 | Li$_2$CuCl$_4$ | 0.2 | PPh$_3$ | 0.05 | −15~Room temperature | 73 |
| A1-3 | 4 | Li$_2$CuCl$_4$ | 0.2 | PPh$_3$ | 0.05 | 10~35 | 79 |
| A1-4 | 3 | CuBr | 0.01 | PPh$_3$ | 0.002 | 10~35 | 91 |
| A1-5 | 1.9 | CuBr | 0.03 | PPh$_3$ | 0.006 | 10~35 | 85 |
| A1-6 | 2.3 | CuBr | 0.03 | PPh$_3$ | 0.006 | 10~35 | 92 |
| A1-7 | 2.3 | CuBr | 0.012 | PPh$_3$ | 0.006 | 10~35 | 85 |
| A1-8 | 2.3 | CuBr | 0.006 | PPh$_3$ | 0.006 | 10~35 | 80 |
| A1-9 | 3 | CuBr | 0.03 | PPh$_3$ | 0.006 | 10~35 | 83 |
| A1-10 | 3 | CuBr | 0.03 | P(C$_6$H$_{11}$)$_3$ | 0.006 | 10~35 | 88 |
| A1-11 | 3 | CuBr | 0.03 | P(CH$_3$C$_6$H$_4$)$_3$ | 0.006 | 10~35 | 91 |
| A1-12 | 3 | CuBr | 0.03 | P(CH$_3$OC$_6$H$_4$)$_3$ | 0.006 | 10~35 | 91 |
| A1-13 | 3 | CuBr | 0.03 | P(OEt)$_3$ | 0.006 | 10~35 | 89 |

*Equivalents with respect to one equivalent of an organic electrophilic agent (15-bromopentadecanoic acid)

According to Example A1-1 and reaction conditions described in Table 2, the following compounds were produced.

Example A1-14

Preparation of 16-methylheptadecanoic acid

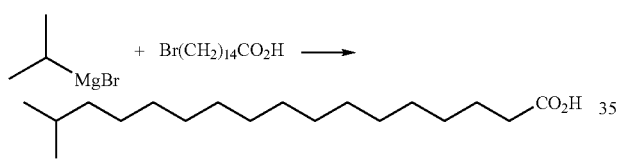

Example A1-15

Preparation of 14-methylpentadecanoic acid

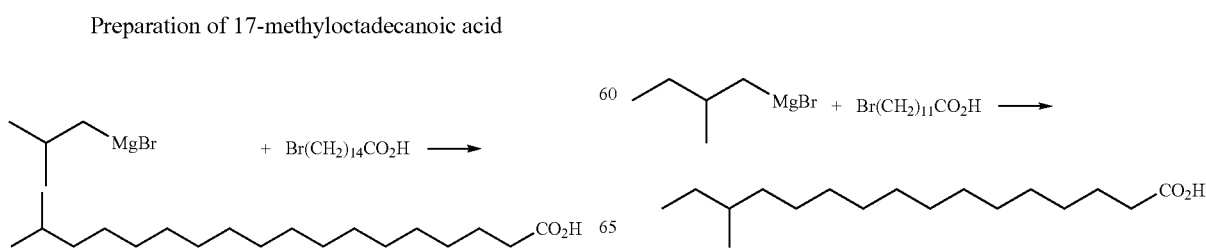

Example A1-16

Preparation of 17-methyloctadecanoic acid

Example A1-17

Preparation of 17-methylnonadecanoic acid

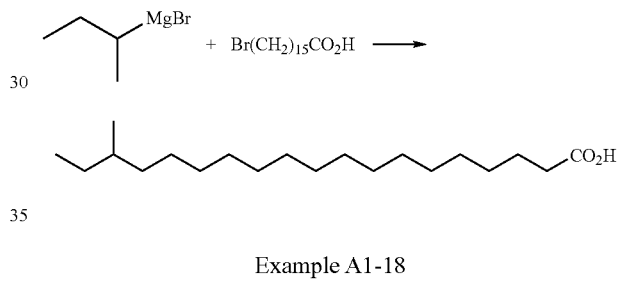

Example A1-18

Preparation of 13-methylpentadecanoic acid

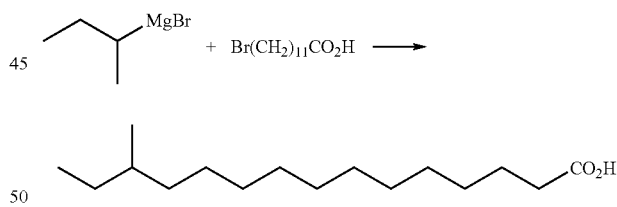

Example A1-19

Preparation of 14-methylhexadecanoic acid

Example A1-20

Preparation of 15-methylhexadecanoic acid

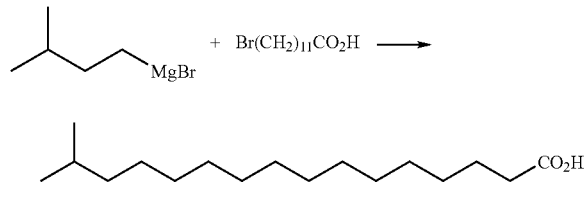

Example A1-21

Preparation of 15-methylheptadecanoic acid

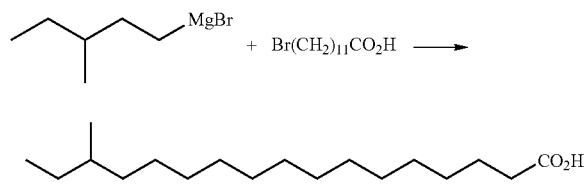

From the results of the Example A1-1 to A1-21 and the Reference examples A1-1 to A1-3, it was verified that a coupling reaction between a bromocarboxylic acid and a Grignard compound is performed well around room temperature in the presence of combination of a copper compound and phosphine or phosphite, and as a result, yield for a desired branched alkyl fatty acid is significantly improved.

Specifically, for a cross-coupling reaction between a Grignard compound and an alkyl halide, when a reaction is carried out in the presence of a copper compound and phosphine or phosphite, a desired cross-coupling compound can be produced with good yield.

Example A2-1

Preparation of 16-methyloctadecanoic acid

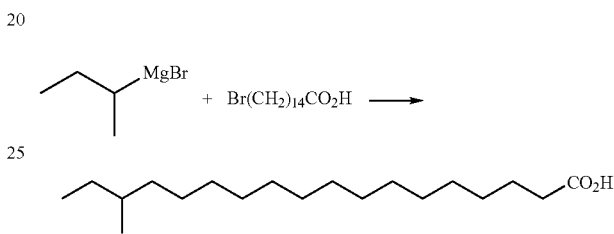

TABLE 2

| Example | Use amount of a Grignard compound* | Copper compound Type | Copper compound Addition amount* | Phosphine Type | Phosphine Addition amount* | Reaction temperature (° C.) | Yield (%) |
|---|---|---|---|---|---|---|---|
| A1-14 | 3 | CuBr | 0.03 | PPh$_3$ | 0.006 | 10~35 | 70 |
| A1-15 | 2.5 | CuBr | 0.03 | PPh$_3$ | 0.006 | 10~35 | 77 |
| A1-16 | 2.5 | CuBr | 0.03 | PPh$_3$ | 0.006 | 10~35 | 88 |
| A1-17 | 2.5 | CuBr | 0.03 | PPh$_3$ | 0.006 | 5~35 | 85 |
| A1-18 | 2.5 | CuBr | 0.03 | PPh$_3$ | 0.006 | 5~35 | 87 |
| A1-19 | 2.5 | CuBr | 0.03 | PPh$_3$ | 0.006 | 5~35 | 79 |
| A1-20 | 2.5 | CuBr | 0.03 | PPh$_3$ | 0.006 | 5~35 | 95 |
| A1-21 | 2.5 | CuBr | 0.03 | PPh$_3$ | 0.006 | 5~35 | 92 |

*Equivalents with respect to one equivalent of an organic electrophilic agent (bromocarboxylic acid)

Reference Example A1-1 to A1-3

Preparation of 16-methyloctadecanoic acid

According to the Example A1-1, the title compounds were produced without adding the phosphine or phosphite as shown in Table 3.

TABLE 3

| Reference example | Use amount of a Grignard compound* | Copper compound Type | Copper compound Addition amount* | Phosphine or phosphite Type | Phosphine or phosphite Addition amount* | Reaction temperature (° C.) | Yield (%) |
|---|---|---|---|---|---|---|---|
| A1-1 | 4 | Li$_2$CuCl$_4$ | 0.2 | — | — | −15~Room temperature | 14 |
| A1-2 | 4 | Li$_2$CuCl$_4$ | 0.2 | — | — | 10~35 | 15 |
| A1-3 | 3 | CuBr | 0.03 | — | — | 10~35 | 45 |

*Equivalents with respect to one equivalent of an organic electrophilic agent (15-bromopentadecanoic acid)

To a four-necked 50 mL of flask equipped with a refluxing condenser tube, a 10 mL of dropping funnel, a magnetic stirrer and a temperature sensor, 15-bromopentadecanoic acid of 1.01 g (3.14 mmol) and 18-crown-6 of 823.3 mg (1.0 eq) were added and dried under reduced pressure. Under argon atmosphere, copper bromide (I) of 13.3 mg (0.03 eq) and anhydrous tetrahydrofuran of 6 mL were added to dissolve the materials. At room temperature, sec-butyl magnesium bromide of 7.85 mL (2.5 eq, 1.0M tetrahydrofuran solution) was added dropwise thereto over thirty minutes. After stirring for one hour, 5 mL of 6N aqueous sulfuric acid solution was added and the extraction was carried out by using 10 mL of hexane. After washing twice with 10 mL ion exchange water, the mixture was dried over magnesium sulfate. After the filtration, the crude product (0.84 g) was obtained by concentration under reduced pressure.

Gas chromatography (column: Ultra-2 manufactured by Agilent Technologies Inc., 30 m×0.2 mm×0.33 μm, DET 300° C., INJ 300° C., column temperature 100° C.→300° C., 10° C./min) was carried out. As a result, the yield was 95%.

Example A2-2 to A2-6

Preparation of 16-methyloctadecanoic acid

16-Methyloctadecanoic acid was produced in the same manner as Example A2-1 except that the copper compound and crown ether shown in the Table 4 below were used.

TABLE 4

| Example | Use amount of a Grignard compound* | Copper compound Type | Copper compound Addition amount* | Crown ether Type | Crown ether Addition amount* | Reaction temperature (° C.) | Yield (%) |
|---|---|---|---|---|---|---|---|
| A2-2 | 2.5 | CuBr | 0.03 | 18-crown-6 | 0.006 | 10~35 | 79 |
| A2-3 | 2.5 | CuBr | 0.03 | 18-crown-6 | 1.0 | 10~35 | 79 |
| A2-4 | 2.5 | CuBr | 0.03 | 18-crown-6 | 2.0 | 10~35 | 72 |
| A2-5 | 2.5 | CuBr | 0.03 | 15-crown-5 | 0.006 | 10~35 | 77 |
| A2-6 | 2.5 | CuBr | 0.03 | Dibenzo-18-crown-6 | 0.006 | 10~35 | 76 |

*Equivalents with respect to one equivalent of an organic electrophilic agent (15-bromopentadecanoic acid)

Reference Example A2-1 to A2-3

Preparation of 16-methyloctadecanoic acid

According to the Example A2-1, the title compounds were produced without adding crown ether as shown in Table 5.

TABLE 5

| Reference example | Use amount of a Grignard compound* | Copper compound Type | Copper compound Addition amount* | Crown ether Type | Crown ether Addition amount* | Reaction temperature (° C.) | Yield (%) |
|---|---|---|---|---|---|---|---|
| A2-1 | 4 | Li$_2$CuCl$_4$ | 0.2 | — | — | −15~Room temperature | 14 |
| A2-2 | 4 | Li$_2$CuCl$_4$ | 0.2 | — | — | 10~35 | 15 |
| A2-3 | 3 | CuBr | 0.03 | — | — | 10~35 | 45 |

*Equivalents with respect to one equivalent of an organic electrophilic agent (15-bromopentadecanoic acid)

From the results of the Example A2-1 to A2-6 and the Reference examples A2-1 to A2-3, it was verified that a coupling reaction between sec-butyl magnesium bromide and 15-bromopentadecanoic acid is performed well around room temperature in the presence of a crown ether and copper bromide (I), and as a result, yield for a desired branched alkyl fatty acid is significantly improved.

Specifically, for a cross-coupling reaction between a Grignard compound and an alkyl halide, when a reaction is carried out in the presence of crown ether compound and a copper compound, a desired cross-coupling compound can be produced with good yield.

Example B-1

Preparation of 15-bromopentadecanoic acid

15-Pentadecanolide of 14.3 g (59.5 mmol) and 32% hydrogen bromide/acetic acid solution of 24.8 g (98.0 mmol, 1.6 eq) were added to 100 mL of autoclave protected with Teflon (registered trade name). After purging with nitrogen and sealing, the autoclave was placed in an oil bath at 120° C. and stirring was carried out for 16 hours. For the stirring, a magnetic stirrer was used. After cooling, 14 mL of water was added, and by using 200 mL of ethyl acetate the mixture was transferred to a separatory funnel. The ethyl acetate layer was analyzed by capillary GC. As a result, it was found that the starting materials disappeared and only the peak of the target compound, i.e., 15-bromopentadecanoic acid, was observed. After washing with saturated brine, the resultant was dried over the magnesium sulfate. After filtration and concentration under reduced pressure, 17.1 g of the target compound was obtained by crystallization using a mixture solvent containing ethyl acetate and n-hexane (yield 90%).

Example B-2

Preparation of 15-bromopentadecanoic acid

15-Pentadecanolide of 14.3 g (59.5 mmol), and 32% hydrogen bromide/acetic acid solution of 24.8 g (98.0 mmol, 1.6 eq) were added to 100 mL of autoclave protected with Teflon (registered trade name). After purging with nitrogen and sealing, the autoclave was placed in an oil bath at 60° C. and stirring was carried out for 16 hours. For the stirring, a magnetic stirrer was used. After cooling, 14 mL of water was added, and by using 200 mL of hot hexane the mixture was transferred to a separatory funnel. After washing with ion exchange water, it was dried over the magnesium sulfate. After filtration, 17.4 g of the target compound was obtained by crystallization using n-hexane (yield 91%).

Example B-3

Preparation of 15-bromopentadecanoic acid (Open System)

To a two-necked 50 mL of flask equipped with a refluxing condenser tube and a magnetic stirrer, 15-pentadecanolide of 1.0 g (4.2 mmol), and 32% hydrogen bromide/acetic acid solution of 3.3 g (13.1 mmol, 3.1 eq) were added. The flask was placed in an oil bath at 60° C. and stirring was carried out for 16 hours under nitrogen atmosphere. Sampling analysis based on GC indicated that area percentage consisted of the target compound 15-bromopentadecanoic acid 10%, the starting material 15-pentadecanolide 89% and byproduct 15-acetoxypentadecanoic acid 1%. Further, after heating and stirring in an oil bath at 80° C. for 8 hours, the area percentage consisted of the target compound 31%, the starting material 65% and byproduct 4%. Further, after heating and stirring in an oil bath at 100° C. for 20 hours, the area percentage consisted of the target compound 42%, the starting material 52%, and by product 6%. Still further, after 32% hydrogen bromide/acetic acid solution 3 g (11.9 mmol, 2.8 eq) were added and then the resultant was heated and stirred in an oil bath at 100° C. for 2 hours, the area percentage consisted of the target compound 47%, the starting material 47%, and byproduct 6%.

Example C-1

Preparation of 16-methyloctadecanoic acid

Step (a)

15-Pentadecanolide of 14.3 g (59.5 mmol) and 32% hydrogen bromide/acetic acid solution of 24.8 g (98.0 mmol, 1.6 eq) were added to 100 mL of autoclave protected with Teflon (registered trade name). After purging with nitrogen and sealing, the autoclave was placed in an oil bath at 60° C. and stirring was carried out for 16 hours. For the stirring, a magnetic stirrer was used. After cooling, 14 mL of water was added, and by using 200 mL of hot hexane the mixture was transferred to a separatory funnel. After washing with ion exchange water, it was dried over the magnesium sulfate. After filtration, 17.4 g of the target compound was obtained by crystallization using n-hexane (yield 91%).

Step (b)

Next, to a four-necked 50 mL of flask equipped with a refluxing condenser tube, a 10 mL of dropping funnel, a magnetic stirrer and a temperature sensor, 15-bromopentadecanoic acid of 800 mg (2.5 mmol) obtained from the above and triphenyl phosphine (Kanto Chemical Co., Inc.) of 3.9 mg (0.006 eq) were added and dried under reduced pressure. Under argon atmosphere, copper bromide (I) (Aldrich Corporation) of 11 mg (0.03 eq) and anhydrous tetrahydrofuran of 1 mL were added to dissolve the materials. At room temperature, 5.5 mL of sec-buthyl magnesium bromide (3 eq, 1.36N tetrahydrofuran solution) were added dropwise thereto over one hour. After stirring for one hour, 10 mL of 1N aqueous hydrochloric acid solution was added and the extraction was carried out twice by using 50 mL of hexane. After washing twice with 10 mL of ion exchange water, the mixture was dried over magnesium sulfate. After the filtration, the crude product (726 mg) was obtained by concentration under reduced pressure.

Quantitation was carried out based on gas chromatography (column: Ultra-2 manufactured by Agilent Technologies Inc., 30 m×0.2 mm×0.33 μm, DET 300° C., INJ 300° C., column temperature 100° C.→300° C., 10° C./min) using octadecane as an internal standard. As a result, the yield was 93%. The total yield from 15-pentadecanolide was 84%.

Example C-2

Preparation of 16-methyloctadecanoic acid

By carrying out the Step (a) according to the operation process as described below and the Step (b) in the same manner as the Example C-1, 16-methyloctadecanoic acid was produced.

15-Pentadecanolide of 14.3 g (59.5 mmol), and 32% hydrogen bromide/acetic acid solution of 24.8 g (98.0 mmol, 1.6 eq) were added to 100 mL of autoclave protected with Teflon (registered trade name). After purging with nitrogen and sealing, the autoclave was placed in an oil bath at 120° C. and stirring was carried out for 16 hours. For the stirring, a magnetic stirrer was used. After cooling, 14 mL of water was added, and by using 200 mL of ethyl acetate the mixture was transferred to a separatory funnel. The ethyl acetate layer was analyzed by capillary GC. As a result, it was found that the starting materials disappeared and only the peak of the target compound, i.e., 15-bromopentadecanoic acid, was observed. After washing with saturated brine, it was dried over the magnesium sulfate. After filtration and concentration under reduced pressure, 17.1 g of the target compound was obtained by crystallization using a mixture solvent containing ethyl acetate and n-hexane (yield 90%).

By using the 15-bromopentadecanoic acid synthesized from the above, the Step (b) was carried out in the same manner as the Example C-1. As a result, 16-methyloctadecanoic acid was produced from 15-pentadecanolide with total yield of 84%.

Example C-3

Preparation of 16-methyloctadecanoic acid (Step (a): Open System)

By carrying out the Step (a) according to the operation process as described below and the Step (b) in the same manner as the Example C-1, 16-methyloctadecanoic acid was produced.

To a two-necked 50 mL of flask equipped with a refluxing condenser tube and a magnetic stirrer, 15-pentadecanolide of 1.0 g (4.2 mmol) and 32% hydrogen bromide/acetic acid solution of 3.3 g (13.1 mmol, 3.1 eq) were added. The flask was placed in an oil bath at 60° C. and stirring was carried out for 16 hours under nitrogen atmosphere. Sampling analysis based on GC indicated that area percentage consisted of the target compound 15-bromopentadecanoic acid 10%, the starting material 15-pentadecanolide 89% and byproduct 15-acetoxypentadecanoic acid 1%. Further, after heating and stirring in an oil bath at 80° C. for 8 hours, the area percentage consisted of the target compound 31%, the starting material 65% and byproduct 41. Further, after heating and stirring in an oil bath at 100° C. for 20 hours, the area percentage consisted of the target compound 42%, the starting material 52%, and by product 6%. Still further, after 32% hydrogen bromide/acetic acid solution of 3 g (11.9 mmol, 2.8 eq) were added and the mixture was then heated and stirred in an oil bath at 100° C. for 2 hours, the area percentage consisted of the target compound 47%, the starting material 47% and byproduct 6%.

By using the 15-bromopentadecanoic acid synthesized from the above, the Step (b) was carried out in the same manner as the Example C-1. As a result, 16-methyloctadecanoic acid was produced from 15-pentadecanolide with total yield of 42%.

Example C-4 to C-21

Preparation of 16-methyloctadecanoic acid

By carrying out the Step (a) in the same manner as the Example C-1 and the Step (b) in the same manner as the Example C-1 by using only the copper compound, the copper compound and phosphine or phosphite, or the copper compound and the crown ether as shown in Table 6 below, 16-methyloctadecanoic acid was produced.

Example C-22 to C-29

Preparation of a Branched Fatty Acid

According to the Example C-1 and by using the cyclic esters and Grignard compounds (2.5 eq) described in Table 7, each of the following compounds was produced.

Example C-22

Preparation of 16-methylheptadecanoic acid

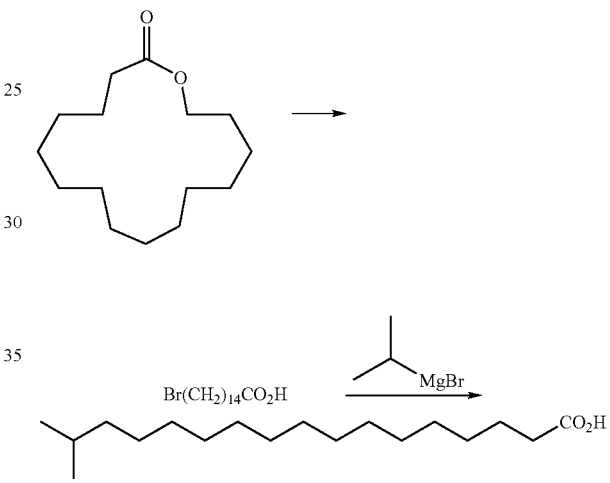

TABLE 6

| Example | Use amount of a Grignard compound* | Copper compound Type | Addition amount* | Additive Type | Addition amount* | Reaction temperature (° C.) | Total yield for the two steps (%) |
|---|---|---|---|---|---|---|---|
| C-4 | 3 | CuBr | 0.03 | — | — | 10~35 | 41 |
| C-5 | 4 | Li$_2$CuCl$_4$ | 0.2 | PPh$_3$ | 0.05 | −15~Room temperature | 66 |
| C-6 | 4 | Li$_2$CuCl$_4$ | 0.2 | PPh$_3$ | 0.05 | 10~35 | 65 |
| C-7 | 3 | CuBr | 0.01 | PPh$_3$ | 0.002 | 10~35 | 82 |
| C-8 | 1.9 | CuBr | 0.03 | PPh$_3$ | 0.006 | 10~35 | 77 |
| C-9 | 2.3 | CuBr | 0.03 | PPh$_3$ | 0.006 | 10~35 | 84 |
| C-10 | 2.3 | CuBr | 0.012 | PPh$_3$ | 0.006 | 10~35 | 77 |
| C-11 | 2.3 | CuBr | 0.006 | PPh$_3$ | 0.006 | 10~35 | 73 |
| C-12 | 3 | CuBr | 0.03 | PPh$_3$ | 0.006 | 10~35 | 76 |
| C-13 | 3 | CuBr | 0.03 | P(C$_6$H$_{11}$)$_3$ | 0.006 | 10~35 | 80 |
| C-14 | 3 | CuBr | 0.03 | P(C$_6$H$_4$CH$_3$)$_3$ | 0.006 | 10~35 | 83 |
| C-15 | 3 | CuBr | 0.03 | P(C$_6$H$_4$OCH$_3$)$_3$ | 0.006 | 10~35 | 83 |
| C-16 | 3 | CuBr | 0.03 | P(OEt)$_3$ | 0.006 | 10~35 | 81 |
| C-17 | 2.5 | CuBr | 0.03 | 18-crown-6 | 0.006 | 10~35 | 72 |
| C-18 | 2.5 | CuBr | 0.03 | 18-crown-6 | 1.0 | 10~35 | 86 |
| C-19 | 2.5 | CuBr | 0.03 | 18-crown-6 | 2.0 | 10~35 | 66 |
| C-20 | 2.5 | CuBr | 0.03 | 15-crown-5 | 0.006 | 10~35 | 70 |
| C-21 | 2.5 | CuBr | 0.03 | Dibenzo-18-crown-6 | 0.006 | 10~35 | 69 |

*Equivalents with respect to one equivalent of an organic electrophilic agent (15-bromopentadecanoic acid)

Example C-23
Preparation of 17-methyloctadecanoic acid
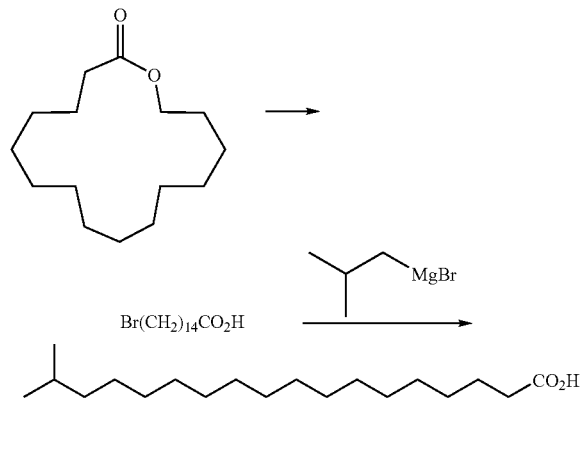
Example C-24
Preparation of 17-methylnonadecanoic acid
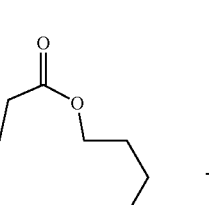
Example C-25
Preparation of 18-methylnonadecanoic acid
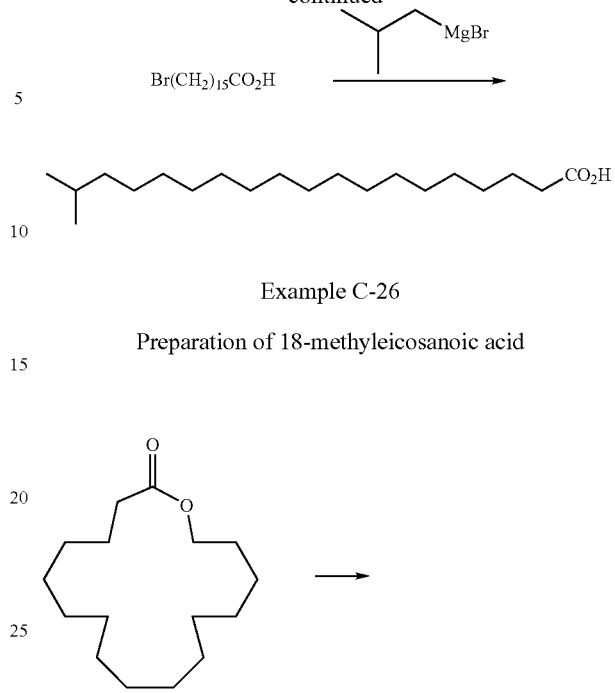
Example C-26
Preparation of 18-methyleicosanoic acid
Example C-27
Preparation of 19-methyleicosanoic acid Example C-28

Preparation of 19-methylheneicosanoic acid

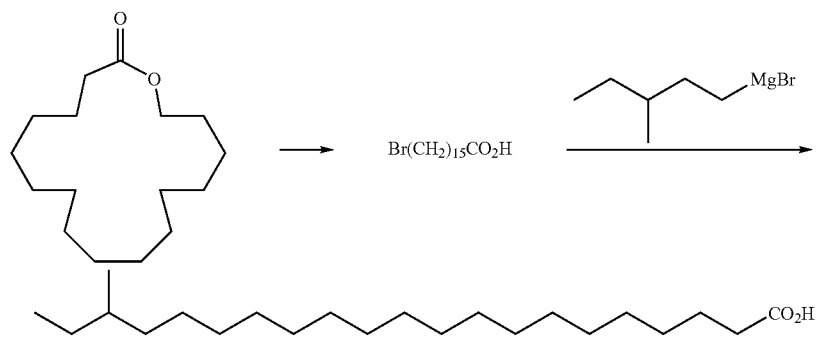

Example C-29

Preparation of 20-methylheneicosanoic acid

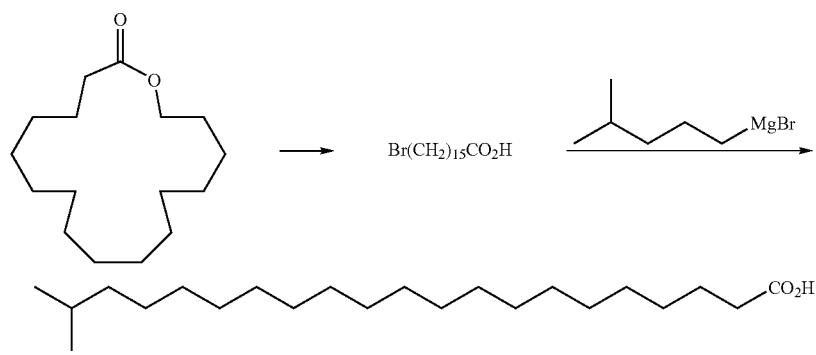

TABLE 7

| Example | Cyclic esters of Step (a) | Yield for Step (a) (%) | Grignard compound of Step (b) | Yield for Step (b) (%) | Total yield for the two steps (%) |
|---|---|---|---|---|---|
| C-22 | 15-Pentadecanolide | 91 | Iso-propyl magnesium bromide | 97 | 88 |
| C-23 | 15-Pentadecanolide | 91 | 2-Methylpropyl magnesium bromide | 99 | 90 |
| C-24 | 16-Hexadecanolide | 90 | Sec-butyl magnesium bromide | 98 | 88 |
| C-25 | 16-Hexadecanolide | 90 | 2-Methylpropyl magnesium bromide | 98 | 88 |
| C-26 | 16-Hexadecanolide | 90 | 2-Methylbutyl magnesium bromide | 97 | 87 |
| C-27 | 16-Hexadecanolide | 90 | 3-Methylbutyl magnesium bromide | 95 | 86 |
| C-28 | 16-Hexadecanolide | 90 | 3-Methylpentyl magnesium bromide | 94 | 85 |
| C-29 | 16-Hexadecanolide | 90 | 4-Methylpentyl magnesium bromide | 93 | 84 |

According to the results of Example C-1 to C-29, it was confirmed that a branched fatty acid can be prepared simply and efficiently from industrially available materials by the production method of the present invention.

The invention claimed is:

1. A method for producing cross-coupling compounds represented by:

wherein $R^1$ represents an alkyl group having 1 to 15 carbon atoms and $R^2$ represents an alkyl group having 1 to 30 carbon atoms with a carboxyl group, said method comprising cross-coupling a Grignard compound represented by:

$R^1MgX$ wherein $R^1$ is as defined in the above, with an alkyl halide represented by:

wherein $R^2$ is as defined in the above, in the presence of a copper compound and a trivalent phosphoric acid compound, a crown ether compound, or a combination thereof.

2. The method according to claim 1, wherein the trivalent phosphoric acid compound is triphenyl phosphine, tris(4-methylphenyl)phosphine, tris(4-methoxyphenyl)phosphine, tricyclohexyl phosphine or tributyl phosphine.

3. The method according to claim 1, wherein the trivalent phosphoric acid compound is triethyl phosphite.

4. The method according to claim 1, wherein $R^1$ is a branched chain alkyl group having 3 to 6 carbon atoms.

5. The method according to claim 1, wherein $R^2$ is a linear chain alkyl group having 5 to 20 carbon atoms with a carboxyl group.

6. A method for producing a ω-bromo long chain carboxylic acid represented by:

$Br—(CH_2)_n—CO_2H$ wherein n represents an integer of 9 to 17, the method comprising:
reacting a cyclic ester with hydrogen bromide in the presence of an acetic acid solvent to obtain the a ω-bromo long chain carboxylic acid;
wherein:
the cyclic ester is represented by formula (1):

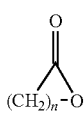

where n is as defined in the above;
the reaction is carried out in a closed system; and
the acetic acid solvent consists of acetic acid and optionally at least one additional solvent selected from the group consisting of tetrahydrofuran, diethyl ether, dimethyl ether, methoxyethane, 1,2-dimethoxy ethane, t-butylmethyl ether, isopropyl ether, dioxane, cyclopentylmethyl ether, hexane, cyclohexane, heptane, isooctane, decane, benzene, toluene, and xylene.

7. The method according to claim 6, wherein the reaction is carried out at a temperature of from 50° C. to 130° C.

8. A method for producing a branched fatty acid having 13 to 26 carbon atoms represented by $R^{1a}—(CH_2)_n—CO_2H$ wherein $R^{1a}$ represents a branched alkyl group having 3 to 8 carbon atoms and n represents an integer of 9 to 17, the method comprising:
reacting a cyclic ester with hydrogen bromide in the presence of an acetic acid solvent to obtain a bromocarboxylic acid; and
reacting the bromocarboxylic acid with a Grignard compound to obtain the branched fatty acid;
wherein:
the cyclic ester is represented by formula (1):

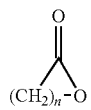

wherein n is as defined in the above;
the bromocarboxylic acid is represented by:

$Br—(CH_2)_n—CO_2H$ wherein n is as defined above;
the Grignard compound is represented by:

$R^{1a}MgX$ wherein $R^{1a}$ is as defined above and X represents a halogen atom;
the bromocarboxylic acid is free of bromocarboxylic acid ester; and
the bromocarboxylic acid is reacted with the Grignard compound in the presence of a copper compound and a trivalent phosphorous compound.

9. The method according to claim 8, wherein the cyclic ester is reacted with hydrogen bromide in the presence of the acetic acid solvent in a closed system.

10. The method according to claim 8, wherein the bromocarboxylic acid is 15-bromopentadecanoic acid or 16-bromohexadecanoic acid.

11. The method according to claim 8, wherein the Grignard compound is sec-butyl magnesium bromide, iso-propyl magnesium bromide, 2-methylpropyl magnesium bromide, 2-methylbutyl magnesium bromide, 3-methylpentyl magnesium bromide, 3-methylbutyl magnesium bromide, or 4-methylpentyl magnesium bromide.

12. The method according to claim 8, wherein the branched fatty acid is 16-methylheptadecanoic acid, 16-methyloctadecanoic acid, 17-methyloctadecanoic acid, 17-methylnonadecanoic acid, 18-methylnonadecanoic acid, 19-methyleicosanoic acid, 19-methylheneicosanoic acid, 20-methylheneicosanoic acid, or 18-methyleicosanoic acid.

13. The method according to claim 2, wherein $R^1$ is a branched chain alkyl group having 3 to 6 carbon atoms.

14. The method according to claim 3, wherein $R^1$ is a branched chain alkyl group having 3 to 6 carbon atoms.

15. The method according to claim 6, wherein the acetic acid solvent consists of acetic acid.

16. The method according to claim 6, further comprising isolating the obtained ω-bromo long chain carboxylic acid after reacting the cyclic ester with hydrogen bromide in the presence of the acetic acid solvent.

17. A method for producing a branched fatty acid having 13 to 26 carbon atoms represented by $R^{1a}—(CH_2)_n—CO_2H$ wherein $R^{1a}$ represents a branched alkyl group having 3 to 8 carbon atoms and n represents an integer of 9 to 17, the method comprising:
reacting a cyclic ester with hydrogen bromide in the presence of an acetic acid solvent to obtain a bromocarboxylic acid; and reacting the bromocarboxylic acid with a Grignard compound to obtain the branched fatty acid;
wherein:
the cyclic ester is represented by formula (1):

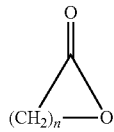 (1)

wherein n is as defined in the above;
the bromocarboxylic acid is represented by:

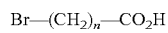

wherein n is as defined above;
the Grignard compound is represented by:

wherein $R^{1a}$ is as defined above and X represents a halogen atom; and
the bromocarboxylic acid is reacted with the Grignard compound in the presence of a copper compound and a crown ether.

18. The method according to claim 17, wherein the cyclic ester is reacted with hydrogen bromide in the presence of the acetic acid solvent in a closed system.

19. The method according to claim 17, wherein the bromocarboxylic acid is 15-bromopentadecanoic acid or 16-bromohexadecanoic acid.

20. The method according to claim 17, wherein the Grignard compound is sec-butyl magnesium bromide, iso-propyl magnesium bromide, 2-methylpropyl magnesium bromide, 2-methylbutyl magnesium bromide, 3-methylpentyl magnesium bromide, 3-methylbutyl magnesium bromide, or 4-methylpentyl magnesium bromide.

21. The method according to claim 17, wherein the branched fatty acid is 16-methylheptadecanoic acid, 16-methyloctadecanoic acid, 17-methyloctadecanoic acid, 17-methylnonadecanoic acid, 18-methylnonadecanoic acid, 19-methyleicosanoic acid, 19-methylheneicosanoic acid, 20-methylheneicosanoic acid, or 18-methyleicosanoic acid.

* * * * *